USOO5326584A

United States Patent [19]
Kamel et al.

[11] Patent Number: 5,326,584
[45] Date of Patent: * Jul. 5, 1994

[54] BIOCOMPATIBLE, SURFACE MODIFIED MATERIALS AND METHOD OF MAKING THE SAME

[75] Inventors: Ihab Kamel, Philadelphia; David B. Soll, Rydall, both of Pa.

[73] Assignees: Drexel University; Ophthalmic Research Corporation, both of Philadelphia, Pa.

[*] Notice: The portion of the term of this patent subsequent to Jan. 14, 2009 has been disclaimed.

[21] Appl. No.: 977,984

[22] Filed: Nov. 18, 1992

Related U.S. Application Data

[63] Continuation-in-part of Ser. No. 820,169, Jan. 13, 1992, Pat. No. 5,260,093, which is a continuation-in-part of Ser. No. 342,270, Apr. 24, 1989, Pat. No. 5,080,924.

[51] Int. Cl.$^5$ .............................................. B05D 3/06
[52] U.S. Cl. .................................. 427/491; 427/534; 427/307; 156/643
[58] Field of Search ................... 427/534, 491, 307, 2; 156/643, 668

[56] References Cited

U.S. PATENT DOCUMENTS

| | | | |
|---|---|---|---|
| 2,999,056 | 9/1961 | Tanner | 522/118 |
| 3,228,741 | 1/1966 | Becker | 351/160 R |
| 3,880,818 | 4/1975 | Shen et al. | 526/322 |
| 3,925,178 | 12/1975 | Gesser et al. | 204/165 |
| 3,944,709 | 3/1976 | Levy | 428/409 |
| 3,959,105 | 5/1976 | Feneberg et al. | 204/165 |
| 3,961,379 | 6/1976 | Highgate | 522/116 |
| 3,985,697 | 10/1976 | Urbach | 523/106 |
| 4,055,378 | 10/1977 | Feneberg et al. | 351/160 |
| 4,072,769 | 2/1978 | Lidel | 427/38 |
| 4,096,315 | 6/1978 | Kubacki | 428/412 |
| 4,099,859 | 7/1978 | Merrill | 351/160 H |
| 4,122,942 | 10/1978 | Wolfson | 206/5.1 |
| 4,123,308 | 10/1978 | Nowlin et al. | 427/41 |
| 4,131,691 | 12/1978 | Morley et al. | 427/41 |
| 4,137,365 | 1/1979 | Wydeven et al. | 428/412 |
| 4,143,949 | 3/1979 | Chen | 427/41 |
| 4,189,364 | 2/1980 | Aelion et al. | 522/4 |
| 4,214,014 | 7/1980 | Hofer et al. | 427/40 |
| 4,240,163 | 12/1980 | Galin | 623/6 |

(List continued on next page.)

FOREIGN PATENT DOCUMENTS 2119957 11/1983 United Kingdom ............ 351/160 R

OTHER PUBLICATIONS

H. Yasuda, "Plasma for Modification of Polymers," *J. Macromol. Sci.-Chem.*, A10(3), pp. 383–420 (1976).

(List continued on next page.)

*Primary Examiner*—Shrive Beck
*Assistant Examiner*—Brian K. Talbot
*Attorney, Agent, or Firm*—Panitch Schwarze Jacobs & Nadel

[57] ABSTRACT

The present invention includes methods of permanently modifying the surface of a substrate material so as to develop a microscopically smooth, biocompatible surface thereon. A portion of the substrate surface is first removed, as by etching, in a radio frequency plasma reactor using inert argon gas. A biocompatible polymeric material may be covalently grafted to the surface of the substrate material by radio frequency plasma-induced grafting. The biocompatible polymeric material is preferably the same as the substrate material but may be different. Alternatively, after etching, the surface of a substrate material may be subjected to radio frequency plasma sufficient to raise the temperature at the substrate surface to just above the glass transition temperature ($T_g$) of the substrate material for a time sufficient to produce a microscopically smooth, biocompatible surface on the substrate material. Further, the present invention includes a prosthesis used in mammals, including an intraocular lens, having a polymeric material core and a biocompatible polymeric material covalently grafted to the polymer core by radio frequency plasma treatment.

19 Claims, 1 Drawing Sheet

U.S. PATENT DOCUMENTS

| | | |
|---|---|---|
| 4,277,595 | 7/1981 | Deichert et al. ............... 528/26 |
| 4,311,828 | 1/1982 | Imada et al. ................... 528/483 |
| 4,312,575 | 1/1982 | Peyman et al. ............. 351/160 H |
| 4,328,257 | 5/1982 | Muehlberger et al. ........... 427/34 |
| 4,344,981 | 8/1982 | Imada et al. ..................... 427/40 |
| 4,405,773 | 9/1983 | Loshaek et al. ............ 526/318.42 |
| 4,409,258 | 10/1983 | Feurer et al. .................... 427/38 |
| 4,430,458 | 2/1984 | Tighe et al. ................... 523/108 |
| 4,463,148 | 7/1984 | Hofer et al. ................... 526/264 |
| 4,478,873 | 10/1984 | Masso et al. .................... 427/40 |
| 4,560,458 | 12/1985 | Ueno et al. ................... 204/165 |
| 4,632,842 | 12/1986 | Karwoski et al. ................ 427/2 |
| 4,656,083 | 4/1987 | Hoffman et al. ................ 427/41 |
| 4,718,907 | 1/1988 | Karwoski et al. .............. 623/12 |
| 4,720,512 | 1/1988 | Hu et al. ........................ 523/112 |
| 4,731,080 | 3/1988 | Galin ................................ 623/6 |
| 4,865,870 | 9/1989 | Hu et al. ............................ 427/2 |
| 4,885,077 | 12/1989 | Karakelle et al. .............. 427/41 |
| 4,919,659 | 4/1990 | Horbett et al. .................... 427/2 |
| 4,927,676 | 5/1990 | Williams et al. ................... 427/2 |
| 5,002,582 | 3/1991 | Guire et al. ..................... 623/66 |
| 5,080,924 | 1/1992 | Kamel et al. ................ 427/412.3 |
| 5,091,240 | 2/1992 | Ratner et al. ..................... 427/2 |
| 5,093,152 | 3/1992 | Bonet et al. .................... 427/307 |

OTHER PUBLICATIONS

Knight et al., "Surface Modification of Intraocular Lenses to Reduce Corneal Endothelial Damage," *AM Intra-Ocular Implant Soc. J*-vol. V, pp. 123-130, Apr. 1979.

Gazard et al., "Lithographic Technique Using Radiation-Induced Grafting of Acrylic Acid into Poly(-Methyl Methacrylate)Films," *Polymer Engineering and Science*, vol. 20, No. 16, pp. 1069-1072 (1980).

K. L. Mittal, "Interfacial Chemistry and Adhesion: Recent Developments and Prospects," *Pure & Appl. Chem.*, vol. 52, pp. 1295-1305 (1980).

Akovali et al., "Polymerization of Hexamethyldisiloxane by Plasma on Activated Charcoal: Investigation of Parameters," *Journal of Applied Polymer Science*, vol. 29, pp. 2617-2625 (1984).

Liu et al., "Polymethyl Methacrylate Resist Sensitivity Enhancement in X-Ray Lithography by In Situ Polymerization," *Appl. Phys. Lett.*, 44(10), pp. 973-975, May 15, 1984.

Keates et al., "Coated Intraocular Lenses," *Ophthalmic Surgery*, vol. 18, No. 9, pp. 693-697 (1987).

BIOCOMPATIBLE, SURFACE MODIFIED MATERIALS AND METHOD OF MAKING THE SAME

CROSS-REFERENCE TO RELATED APPLICATIONS

This is a continuation-in-part application of our co-pending U.S. patent application Ser. No. 07/820,169, now U.S. Pat. No. 5,260,093 filed Jan. 13, 1992, which is a continuation-in part of application Ser. No. 07/342,270, filed Apr. 24, 1989 now U.S. Pat. No. 5,080,924.

FIELD OF THE INVENTION

The present invention relates to methods of permanently modifying the surface of materials by plasma-induced and, where desired, post-plasma reactions to produce biocompatible, surface modified materials. In addition, the present invention relates to biocompatible, surface modified prostheses and, in particular, to a biocompatible, surface modified intraocular lens used in mammals.

BACKGROUND OF THE INVENTION

Prosthetic devices or prostheses are commonly used in medical procedures to replace or augment defective organs in mammals and humans. Such prostheses are numerous and diverse in structure and application. Examples of prostheses include artificial joints, valve replacements, artificial skin, vascular grafts, shunts, plates and contact and intraocular lenses. Typical prosthetic materials include metals, ceramics, silicone rubbers, polyesters, polyurethanes and/or polysulfones. Synthetic polymers, such as polymethylmethacrylate (PMMA), silicone elastomers and polymers of hydroxyethylmethacrylate (HEMA), are preferred polymers for prosthetic use in general and contact lenses and intraocular lenses in particular.

PMMA has several beneficial characteristics for prosthetic use, including excellent light transmission capability, good optical clarity, resistance to fluid diffusion and in vivo deterioration, ease in processing (injection molding or machining, for example) and ease in implantation.

A problem with typical prior prostheses, such as lens prostheses, is that they are manufactured by machining and also some by injection molding. In the former, the machining process typically leaves circular lathe marks or grooves visible at even relatively low magnification. These machining marks render the lens unusable until the lens surface is smoothed, typically by a mechanical polishing process. However, conventional polishing processes generally take several days to complete, have failure rates in excess of 30% and fail to produce a microscopically smooth surface. The surfaces of injection molded lenses do not show machine lathe marks. However, their surfaces are also not microscopically smooth and reflect the surface finish of the mold.

Also, typical prosthetic devices comprise natural and/or synthetic materials which are highly irregular on the cellular level. These rough prostheses, especially those which are implanted, can cause tissue irritation, cell proliferation, edema and scarring. For example, posterior lens capsule opacification is a prevalent problem among those patients who have received intraocular lens implants comprising conventionally polished PMMA and other similar materials. Pseudophakic precipitates on the surfaces of an intraocular lens can be indicative of microscopic surface irregularities.

It is desirable to modify the surface properties of such abrasive materials without changing the beneficial characteristics thereof by developing a microscopically smooth surface to discourage tissue adhesion and inhibit unwanted cellular growth. Prostheses which do not promote tissue adhesion, which inhibit cellular growth, and which are not otherwise toxic to living systems may be considered "biocompatible." The biocompatible modified surface should be resistant to deterioration over time and should have no adverse effects on contacting tissues and cells.

Those skilled in the art have long recognized the need for biocompatible, surface modified materials for use in prosthetic devices and other materials. For example, U.S. Pat. No. 3,961,379 discloses a bioimplantable device manufactured from a cross-linked, swollen, hydrophilic polymer. These modified polymers must be solid and must be swellable by fluid swelling substances. Once swollen, the solid polymer is polymerized with a modifying substance by, for example, high energy particle radiation.

U.S. Pat. No. 4,189,364 discloses hydrophilic polymers formed in situ by irradiating a mixture of hydroxyalkyl methacrylate and a cross-linking agent. This patent discloses a process for forming hydrophilic polymer articles or hydrophilic polymer coatings on other substrates, such as glass or plastic, by polymerizing a hydrophilic monomer system by high energy particulate irradiation, such as accelerated electrons or nuclear particles including neutrons, protons, alpha, beta and/or gamma particles.

Radiation-induced grafting of acrylic acid onto other polymer films is disclosed by Gazard, M. et al., "Lithographic Technique Using Radiation-Induced Grafting of Acrylic Acid Into Poly(Methyl Methacrylate) Films," *Polymer Engineering and Science*, 20:16 (1980). Gazard et al. disclose that, under ionizing radiation, polymer properties, such as solubility, may be modified. Ionizing radiation of polymers leads to the formation of free radicals and other intermediates, which may be used to initiate the grafting of a monomer to produce a grafted copolymer with properties different from those of the initial polymer. For example, a grafted copolymer of irradiated PMMA and acrylic acid is insoluble in solvents of PMMA.

U.S. Pat. No. 2,999,056 also discloses that an unsaturated organic acid may be attached to a shaped polymeric structure by ionizing radiation.

Other methods of altering the surface of polymeric objects include exposing the surface of a polymeric article to low temperature plasma or an electrically charged gaseous atmosphere, followed by contacting the surface of the polymeric article with a surface modifying compound as described, for example, in U.S. Pat. No. 4,344,981. This two-step method is generally called plasma-induced coating. Plasma induction has been described generally in U.S. Pat. No. 4,328,257, Yasuda, "Plasma for Modification of Polymers," *J. Macromol. Sci. C. Chem.*, 10(3):383 (1978), Mittal, "Interfacial Chemistry and Adhesion: Recent Developments and Prospects," *Pure & Appl. Chem.*, 52: 1295 (1980), Akovali, G. and Hasirci, N., "Polymerization of Hexamethyldisiloxane by Plasma on Activated Charcoal: Investigation of Parameters," *J. Appl. Polymer Sci.*, 29:2617 (1984) and Liu, W. T. et al., "Polymethyl Methacrylate Resist Sensitivity Enhancement in X-Ray Lithography by In Situ Polymerization," *Appl. Phys. Lett.,* 44:973 (1984), for example.

Ionized vapor or a plasma discharge is typically created in a vacuum chamber in which the object to be modified is placed. The plasma discharge conditions the surface of the object by creating free radicals and/or ions. It is known, for example, that exposing the surface of an object to a plasma discharge, such as an oxygen plasma, enhances the wettability or hydrophilicity of such a surface. However, such treatment is only temporary. U.S. Pat. Nos. 3,925,178; 3,944,709; 4,072,769; 4,096,315; 4,122,942; 4,123,308; 4,131,691; 4,137,365; 4,214,014 and 4,478,873 disclose examples of polymers whose surface characteristics have been modified by a plasma discharge.

Plasma discharge treatment may also be used to prepare an object for the attachment or grafting of a compound or material to the plasma discharge treated object. For example, a plasma discharge step may be used to condition the surface for grafting by creating free radicals to which a compound or material may be grafted. Such compounds or materials are generally called surface modifiers. Knight, P.M. et al., in "Surface Modification of Intraocular Lenses to Reduce Corneal Endothelial Damage, "*Am. Intra-ocular Implants Soc. J.,* 5:123 (1979) disclose one example of a polymer object having a surface modifier attached thereto using gamma irradiation and radio frequency (RF) gas plasma treatment to generate free radicals on the surface of a PMMA intraocular lens followed by polymerizing hydrophilic monomers, in particular, HEMA and vinyl pyrrolidone, as a coating on the surface of the lens. While the coated surfaces exhibited enhanced hydrophilicity, the coated surfaces were not stable when sterilized by boiling. Surface modification by gamma radiation followed by polymerization on the surface, on the other hand, remained intact through several hours of boiling. However, such coated PMMA surfaces were damaging to rabbit endothelial cells and surfaces coated with dissolvable coatings, such as polyvinyl acetate, were preferred.

Another example of a surface treated polymer is disclosed in U.S. Pat. No. 4,312,575. This patent discloses a soft, highly oxygen permeable, hydrophobic polymeric lens which has a surface coating of an ultra-thin, optically clear, permeable barrier. The coating is the reaction product resulting from a glow discharge polymerization process conducted in a hydrocarbon or halogenated hydrocarbon gaseous atmosphere. While the plasma discharge process, itself, results in a hydrophilic surface, this patent discloses that subsequent exposure to a glow discharge atmosphere of oxygen or ambient oxygen yields a still more hydrophilic surface.

U.S. Pat. No. 4,409,258 discloses a method for rendering contact lenses hydrophilic by bombarding the lens of PMMA or silicone, for example, with a positive ion beam generated by a plasma discharge, such as an oxygen plasma. The lens is thereafter hydrated, preferably at an elevated temperature.

Examples of surface treated polymeric lenses for use in humans are included in U.S. Pat. No. 3,880,818. This patent discloses a soft contact lens that is flexible and physiologically compatible. The lens is made by manufacturing a hard, inflexible prepolymer, such as a hard acrylic acid-type polymer, and reacting the inflexible prepolymer with an alcohol to esterify pendant carboxyl groups with alkyl groups, hydroxy alkyl groups or alkoxyalkyl groups, containing no more than eleven carbon atoms.

U.S. Pat. No. 4,143,949 discloses a discharge polymerization and coating process for making a hydrophilic contact lens from an oxygen permeable, hydrophobic polymer. The hydrophobic lens is placed in a glow discharge apparatus containing an atmosphere comprising a polymerizable organic monomer, such as hydroxyalkyl acrylate or methacrylate, glycidyl methacrylate, propylene oxide or N-vinyl-2-pyrrolidone. The glow discharge is used to polymerize the monomer onto the surface of the contact lens.

Other examples of surface treated polymeric objects include U.S. Pat. Nos. 3,228,741; 3,959,105; 3,985,697; 4,055,378; 4,277,595; 4,405,773; 4,430,458; 4,463,148; and 4,731,080. U.S. Pat. No. 4,731,080, for example, discloses a coated intraocular lens having a hydrophobic cross-linked vinyl-containing silicone polymer placed on the lens surface in solution.

It would be desirable to have a biocompatible, surface modified material and a method for producing the same, wherein the surface of the substrate material is cleaned, and active species, such as ions and free radicals, are produced on the surface by a plasma treatment to enhance subsequent grafting of a polymeric biocompatible material to the substrate surface to provide a substantially permanent, smooth surface on a cellular level. A method for grafting a polymeric biocompatible material to the surface of a substrate is disclosed in our U.S. Patent No. 5,080,924 and U.S. Pat. No. 5,260,093 the disclosures of which are incorporated herein by reference. By pretreating the surface of the substrate material, the smoothness of the substrate and the grafted surface may be improved.

BRIEF DESCRIPTION OF THE INVENTION

According to the present invention, a method is provided for permanently modifying a surface of a polymeric substrate material so that the substrate material develops a microscopically smooth, biocompatible surface. The method comprises removing at least a portion of the surface of the polymeric substrate material and covalently grafting a biocompatible polymeric material to the surface of the substrate material by radio frequency plasma treatment. The biocompatible polymeric material comprises substantially the same material as the polymeric substrate.

Another aspect of the present invention is another method for permanently modifying a surface of a substrate polymeric material. The method comprises the steps of removing at least a portion of the surface of the polymeric substrate material by subjecting the substrate surface to inert gas radio frequency plasma sufficient to raise the temperature at the substrate surface to just above the glass transition temperature of the substrate material for a time sufficient to produce surface relaxation and a resulting microscopically smooth, biocompatible surface on the substrate material.

Yet another aspect of the present invention is a prostheses used in mammals which has a permanently modified microscopically smooth, biocompatible surface. The prostheses comprises a polymeric material core having an etched surface and a biocompatible material grafted to the surface of a polymer core by radio frequency plasma treatment. The biocompatible polymeric material comprises substantially the same material as the core.

Another aspect of the present invention is an intraocular lens having a permanently modified, smooth, biocompatible surface. The lens comprises a polymeric material lens body having an etched surface and a biocompatible polymeric material. The biocompatible polymeric material is grafted to the surface of the lens body and comprises substantially the same material as the body.

A further aspect of the present invention is a method of manufacturing a prostheses to provide the prostheses with a microscopically smooth, biocompatible surface without the use of mechanical polishing. The method comprises the steps of etching a surface of a polymeric prostheses core and covalently grafting a polymeric biocompatible material to the surface of the core by radio frequency plasma treatment.

BRIEF DESCRIPTION OF THE DRAWING

The foregoing summary, as well as the following detailed description of the preferred embodiments, will be better understood when read in conjunction with the appended drawing. For the purpose of illustrating the invention, there is shown in the drawing one embodiment, it being understood, however, that the invention is not limited to the specific method and instrumentality disclosed. In the drawing.

DETAILED DESCRIPTION OF PREFERRED EMBODIMENTS

Figure 1:
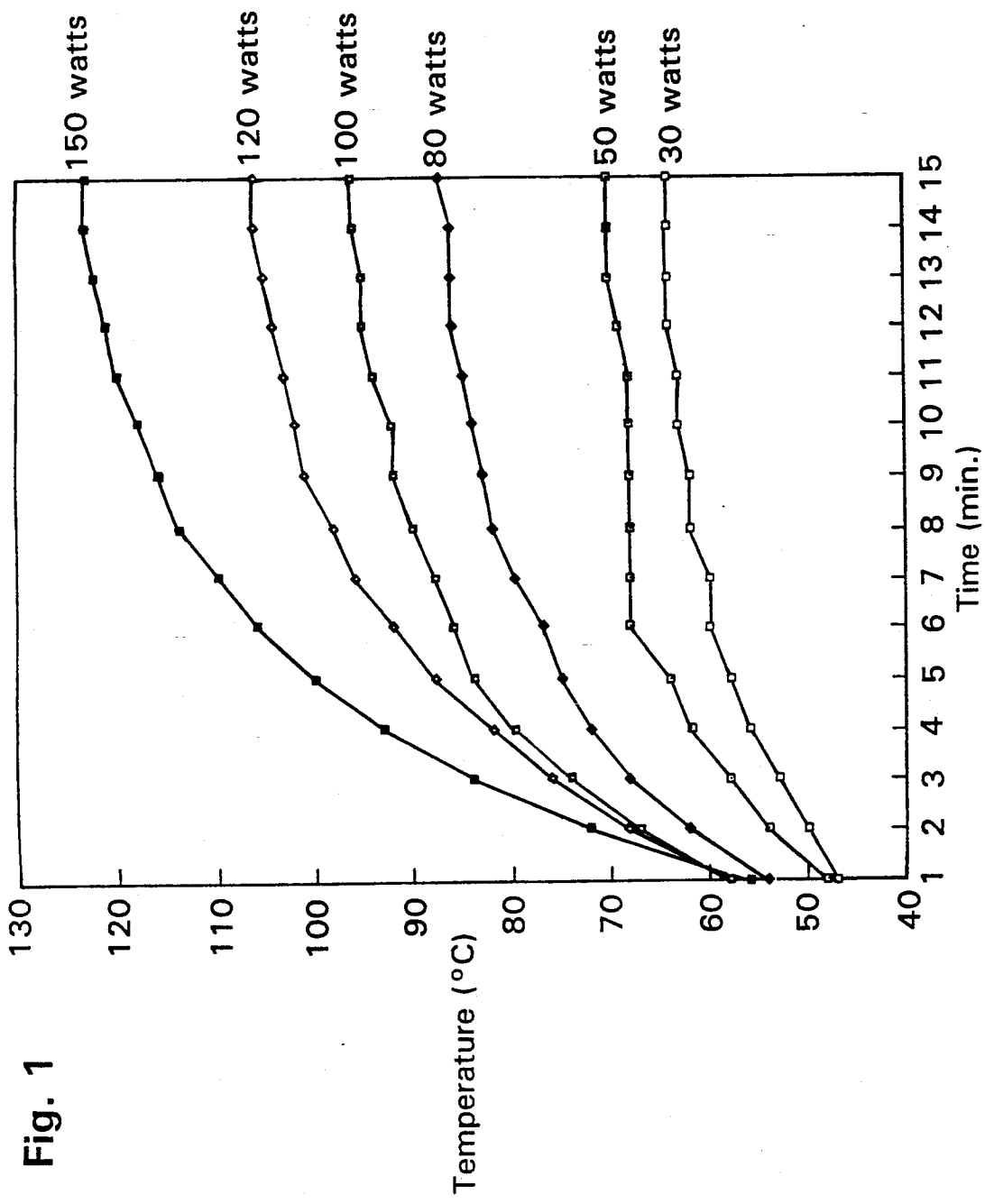
FIG. 1 is a graph of surface temperature of PMMA substrates as a function of time at various radio frequency power levels which shows the thermal annealing effect of argon plasma where the temperature of the substrate surface increases with plasma power and can be made to exceed the glass transition temperature, according to one embodiment of the present invention.

Although the methods of modifying the surface of a polymeric substrate material according to the present invention apply generally to many different materials, the methods are described and examples are given below for polymeric intraocular lenses as prostheses which may be used in mammals. It will be understood by one of ordinary skill in the art that the methods of the present invention may be used to prepare permanently modified surfaces of other substrate materials, such as those prosthestic materials identified above. Moreover, it will be apparent to an ordinary skilled artisan that the methods of the present invention readily lend themselves to the preparation of materials having modified or enhanced surface characteristics having other uses.

Examples of polymeric substrate materials which are useful in the present invention include polymers, such as silicone elastomers, polypropylene, polyesters, such as polyethylene terephthalate, polytetrafluoroethylene, polyurethane, ethylenediamine, PMMA, ethylenediamine, polyacrylic acid, and polymers of HEMA, ethylenediamine, diethylenetriamine, allylamine hexamethyldisiloxane, silazane and N-vinyl pyrrolidone.

Generally, the substrate material used in accordance with the present invention is chosen dependent upon its intended use. For example, PMMA, HEMA and silicone are useful for making prosthetic devices intended for implantation or other applications in mammals. However, in view of the present specification, one of ordinary skill in the art will appreciate that any biocompatible organic polymer may be used as a substrate material, as well as certain ceramics. Where an optically clear polymer for use in prosthetic devices for mammals is desired as the substrate material, it is presently preferred that the polymer comprise PMMA or a silicone elastomer.

According to the method of the present invention, at least a portion of the surface of the polymeric substrate material is removed to clean the substrate and produce active species on the polymer surface, such as ions and free radicals, which can be used for inducing a grafted reaction. Preferably, the removal of the portion of the surface material is accomplished by inert gas etching. The etching may be induced in a radio frequency (RF) plasma reactor, such as are well known to those of ordinary skill in the art. The Branson Model 3003-1813 is one example of a suitable radio frequency gas plasma reactor which may be used to etch the surface of the polymeric substrate material. One skilled in the art will appreciate, however, that other plasma reactors and apparatus may be used in accordance with the present invention.

Generally, the rate of material removal is influenced by the frequency or power of the gas plasma, the treatment time, the gas used in the plasma reactor, the gas pressure/concentration and the type of bond present on the treated substrate material surface, depending on the particular substrate material. For the Branson Model 3003-1813 radio frequency plasma reactor, frequency is kept at 13.56 MHz, which is suitable for etching.

Preferably, the etching process includes injecting a noble or ambient gas into the reactor to create ions which bombard the substrate creating active sites on the substrate surface. Nitrogen and ammonia gases are also believed to be useful in the radio frequency gas plasma reaction when nitrogenous compounds are desired. Preferably, the noble gas is argon, which creates active sites on the substrate surface but does not produce new chemical groups when applied to the substrate surface in a RF gas plasma reactor. Where no biocompatible material is to be grafted to the substrate surface (discussed below) or where the presence of new chemical groups on the substrate surface is not desired, it is presently preferred to use a noble gas, such as argon, as the RF gas in the plasma reactor. Oxygen, on the other hand, for example, tends to produce peroxides in such plasma-induced grafting reactions and is, therefore, generally less stable chemically. One of ordinary skill in the art will be readily able to determine in view of this disclosure suitable gases which may be used in the plasma reaction in accordance with the present invention.

The substrate surface to be etched is first cleaned with a mild soap solution, i.e., a 1% sodium decyl sulphate solution, and rinsed in deionized water to remove any contaminants that may be present from the manufacturing processes and subsequent handling. The lens is positioned in the radio frequency plasma reactor on a glass or other suitable fixture. The pressure in the reactor is reduced to less than about 0.05 to about 0.1 torr for about 5 to about 10 minutes. Argon gas is introduced into the chamber at a pressure of about 8 to about 10 psi and the pressure within the reaction chamber is adjusted to about 0.3 to about 0.5 torr for about 5 to about 10 minutes to purge the chamber with the argon gas. Radio frequency power was applied at about 50 to about 200 watts for about 30 to about 60 minutes while maintaining the pressure level at about 0.3 to about 0.5 torr. The RF power supply is discontinued and the chamber is maintained at a pressure of about 0.3 to about 0.5 torr for about 5 to about 10 minutes. One of ordinary skill in the art would understand that the pressure levels, power levels and times may vary based upon such variables as the substrate material, different reactors, and the choice of ambient gas.

In one embodiment of the present method, after etching of the substrate surface, the substrate surface may be subjected to radio frequency plasma sufficient to raise the temperature at the substrate surface to just above the glass transition temperature of the substrate material for a time sufficient to produce a microscopically smooth, biocompatible surface on the substrate material.

While not wishing to be bound by any particular theory, the inventors believe that plasma treatment to induce an increase in temperature causes a thermal annealing at the surface of the substrate whereby irregular surface features (such as surface peaks, etc.) relax, evening out such irregularities.

FIG. 1 is a graph of substrate surface temperature of PMMA substrates as a function of time at several power levels ranging from 30 to 150 watts. As shown in FIG. 1, the temperature of the substrate surface increases during plasma treatment. For example, at 150 watts of power, the temperature of the substrate climbs about 60° C. after 10 minutes of plasma treatment.

Where temperatures above the glass transition temperature are desired, relatively higher radiation power is preferred. For example, to reach a surface temperature of about 105° C., which is the glass transition temperature of PMMA, radiation power of about 120 to about 150 watts is preferred. One skilled in the art may readily determine glass transition temperature by reference to publicly available material characteristic tables and experimentally determine the temperature obtainable at a given wattage in a given reactor. Other temperatures can then be calculated by factoring in time, efficiency of the reaction chamber, the surface area of the substrate and reactor power, for example. The radiation power used and the time the substrate is exposed to such radiation should be such to avoid subsurface thermal circulation and melting of the substrate.

In an alternative embodiment, the method includes a step of covalently grafting a polymeric biocompatible material to the surface of the substrate material by radio frequency plasma treatment. Preferably, the biocompatible polymeric material is introduced in the monomer form and is selected from ethylenediamine, hexamethyldisiloxane, acrylic acid, diethylenetriamine, allylamine, hydroxyethylmethacrylate, methylmethacrylate and combinations thereof, for example.

The resulting biocompatible polymeric material is preferably grafted to the substrate material in a relatively uniform thickness and texture along the surface of the substrate material. In addition, especially where it is desired to use the substrate material as a prosthetic lens, it is preferred that the biocompatible polymeric material is present on the surface of the substrate material in a relatively uniform, small thickness to prevent interference with the optical clarity of the lens. More preferably, the biocompatible polymeric material is present in few molecular layers. In one embodiment of the present invention, for example, a surface modified substrate comprises a biocompatible polymeric material grafted to the surface of a substrate material with a biocompatible polymeric material thickness of about 100 Å.

Grafting of the biocompatible polymeric material according to the present invention is conducted using radio frequency plasma-induced grafting. Other methods of grafting, such as electron beam or ultra-violet (UV) radiation, are not suitable where it is desired to modify only the surface of the substrate material. For example, where a prosthetic lens, such as a contact lens or intraocular lens, is desired to be modified, modification should be confined to the surface of the lens to avoid affecting the optical properties of the lens. Radio frequency plasma-induced grafting according to the present invention avoids structural modification below the outer-most surface layer, and generally results in more desirable optical properties.

Such gas plasma-induced grafting may be conducted in a radio frequency gas plasma reactor such as that discussed above capable of generating a frequency of about 1 MHz to about 40 MHz. The frequency generated by a typical commercial gas plasma reactor is 13.56 MHz, although one skilled in the art will recognize that higher and lower frequencies may be used to graft the biocompatible polymeric material to the surface of the substrate material in a radio frequency gas plasma reactor, depending on the substrate material and biocompatible polymeric material used, the relative ease or difficulty in preparing the surface of the substrate material for grafting, the relative ease or difficulty of vaporizing or polymerizing the biocompatible material, among other factors.

The length of time the biocompatible material in an induced plasma state should be allowed to react with the substrate material depends upon several factors, including the plasma or radiation power, the radio frequency, the flow concentration or pressure, the temperature and the desired thickness of the grafted material. Preferably, the radiation power is about 10 watts to about 200 watts, depending upon the biocompatible material. For example, where the biocompatible material comprises silazane, hexamethyldisiloxane, MMA, NVP or AA, it is presently preferred that the radiation power is about 50 watts. Where the biocompatible layer material comprises HEMA (discussed below), it is presently preferred that the radiation power is about 10 watts to about 200 watts.

In any event, except where desired, the reactor power used and the duration during which such power is used should be low and/or short enough so as to not induce thermal circulation and melt the substrate surface. For example, where the substrate material comprises PMMA, the reaction conditions (i.e., power and duration) should not increase the temperature of the substrate material above about 40°-60° C. One skilled in the art may readily determine, in view of the plasma reaction variables described above, the desired plasma radiation power to be used in accordance with the present invention.

The temperature in the plasma reaction should not be allowed to approach those temperatures which may structurally damage the substrate material or the biocompatible material. High radiation power and any polymerization reaction (i.e., polymerization which may occur when the grafting reaction occurs; e.g.: polymerization to polymethylmethacrylate) tend to increase the temperature of the plasma reaction zone. It is desirable, therefore, to maintain the temperature in the plasma reaction below the temperature at which the substrate material and/or the graft material will be damaged, typically below about 60°-80° C.

The flow concentration or vapor pressure of the plasma reactants in the reactor chamber should be low enough so that the particular monomer of the biocompatible material vaporizes when introduced into the reactor. Preferably, the vapor pressure is about 0.1 torr to about 0.6 torr. More preferably, the vapor pressure is about 0.4 torr.

The plasma reaction is preferably conducted for a period of time of about 1 minute to about 60 minutes. More preferably, the plasma reaction is allowed to occur for a period of time of about 15 minutes to about 30 minutes. The flow of biocompatible material into the reactor chamber may be continued for a period of time after the RF power supply to the reactor is terminated. The continued supply of biocompatible material is believed to quench long-lived radicals that could be present on some substrates.

In view of this disclosure, one skilled in the art may readily determine the reactants, time, pressure and temperature conditions for a reaction using given materials without undue experimentation. For example, in one embodiment of the present invention, methyl methacrylate liquid is introduced into a plasma reactor chamber having a plasma-etched or treated body of PMMA where, because of the low pressure within the chamber, the methyl methacrylate vaporizes. The methyl methacrylate is exposed to about 50 to about 150 watts of radio frequency radiation at about 20°-30° C. where its vapor pressure is about 0.4 to about 0.5 torr.

Where it is desired to have no change in the substrate surface chemistry, the biocompatible polymeric material is substantially the same as the material forming the substrate. Once the substrate material surface has been modified by covalently grafting the biocompatible material to the surface of the substrate material, the modified surface should have properties which are relatively nontoxic and nonirritating to living tissues. In addition, the modified surface should not adversely affect the desired properties of the remainder of the substrate material, such as structural integrity and optical clarity, among others. In addition, the modified surface should be microscopically smooth. As used herein, the term "microscopically smooth" shall mean that the surface of the modified substrate should be featureless upon examination at an enlargement of about 3,000 to about 10,000×, e.g. by SEM microscopy. In addition, where desired, and depending on the properties of the biocompatible polymeric material, the modified surface should show absence of crystallinity, cross-linked and thermally stable. The water contact angle should remain substantially unchanged after grafting of the biocompatible material to the substrate surface.

Where the substrate material is intended for use in or as a prosthetic device, such as an intraocular lens, the surface modification of the present invention should not adversely affect the transparency or ocular acuity of the substrate material. Further, the biocompatible material to be grafted to the substrate surface preferably comprises a material that is relatively easy to polymerize in a gas plasma environment. Such materials include unsaturated compounds or those compounds containing nitrogen, silicone or halogen. Materials that are relatively difficult to polymerize in a gas plasma environment include polymers, cyclic compounds, compounds with a high molecular weight, natural polymers such as proteins, and those compounds with extremely high vapor pressures.

Novel products having a permanently modified surface resulting from the method of the present invention include prostheses, such as an intraocular lens, for use in mammals having a permanently modified, biocompatible surface, which comprises a polymer lens body and a biocompatible, polymeric material grafted thereto, where the biocompatible, polymeric material comprises substantially the same material as the material forming the polymer lens body, such as PMMA.

In addition, novel products produced using the method of the present invention include prostheses for use in mammals comprising a polymeric material substrate having a permanently modified surface where the surface was modified by subjecting the substrate surface to radio frequency plasma sufficient to raise the temperature at the substrate surface to just above the glass transition temperature.

The invention will now be illustrated in further detail by reference to the following specific, non-limiting examples.

EXAMPLE I

An intraocular lens manufactured by Alcon/CILCO from PMMA was abraded using 1 micron aluminum oxide particles to produce grooves on the surface of the lens of 1 micron depth. Macroscopically, the lens had a hazy appearance. The lens was cleaned in a 1% sodium dodecyl sulfate (SDS) solution and then thoroughly rinsed in deionized water to remove any contaminants that may be present from the manufacturing process or subsequent handling. The lens was positioned in a Branson 3000 Series radio frequency plasma reactor in a glass treatment fixture. The pressure inside the reactor was reduced to less than about 0.1 torr for approximately 10 minutes. Argon gas (Ar) was then introduced at approximately 8 psi and the pressure inside the reactor was adjusted to 0.5 torr for 10 minutes to purge the chamber with the argon gas. Radio frequency power was then turned on to 120 watts while maintaining chamber pressure at 0.5 torr. Treatment with the argon gas plasma continued for approximately 60 minutes. After this time, radio frequency power was turned off and the chamber was purged to normal atmospheric pressure to open the chamber door. Macroscopically, the lens appeared clean and clear. Upon microscopic examination, some surface irregularities or memory of the initial grooves was apparent.

EXAMPLE II

An intraocular lens was treated using the procedures of Example I. After turning off the radio frequency power, the chamber was then pumped down to a pressure of 0.1 torr for approximately 5 minutes to evacuate the chamber. Methylmethacrylate (MMA) monomer was then introduced into the reactor chamber at maximum flow rate (approximately 0.8 torr) and radio frequency power was turned on to 70 watts for 30 minutes. After this time, MMA delivery was discontinued and the radio frequency power was shut down. The chamber was then purged to normal atmospheric pressure to open the chamber door. Macroscopically and microscopically, the lens was free of any surface irregularities, surpassing the surface quality of the original, commercial lens.

EXAMPLE III

A PMMA square sample manufactured by ICI Americas, Inc. of Wilmington, Del. had a contact angle of 79°. After abrading the sample using aluminum oxide particles having an average diameter of 1 micron to form 1 micron deep grooves on the sample surface, the contact angle was reduced to 77°. The sample was cleaned with a 1% sodium decyl sulphate solution and rinsed with deionized water. The surface of the sample was etched using a Branson 3003-1813 RF plasma reactor by reducing the pressure in the reactor to less than about 0.1 torr for about 10 minutes and then purging the reactor chamber with argon gas at a pressure of 8 psi and reducing the pressure to about 0.5 torr for about 10 minutes. RF power was applied at about 100 watts for about 30 minutes while the argon pressure level was maintained at about 0.5 torr. The power supply was discontinued and the chamber evacuated to about 0.1 torr for about 5 minutes.

Methylmethacrylate (MMA) monomer was introduced into the reactor to maintain the chamber pressure at about 0.8 torr and the RF power was turned on to 50 watts. After 60 minutes, the MMA delivery and RF power supply were discontinued. The chamber was purged to normal atmospheric pressure. The contact angle of the sample after plasma treatment was 79°, which is equal to the contact angle measured prior to treatment. Therefore, the chemical nature of the surface of the sample was unchanged by grafting the MMA monomer thereto. For purposes of comparison, an untreated Coopervision ™ PMMA intraocular lens has a measured contact angle of 74°.

TABLE I

| Treatment | Contact Angle |
| --- | --- |
| ICI-PMMA sample without plasma treatment | 79° |
| After abrasion | 77° |
| After plasma treatment | 79° |
| Coopervision-PMMA lens without plasma treatment | 74° |

The present invention may be embodied in other specific forms without departing from the spirit or essential attributes thereof and, accordingly, reference should be made to the appended claims, rather than the specification, as indicating the scope of the invention.

We claim:

1. A method of permanently modifying a surface of a polymeric substrate material to produce a microscopically smooth, biocompatible surface thereon, comprising the steps of:
   removing at least a portion of the surface of the polymeric substrate material; and
   covalently grafting a polymeric biocompatible material to the polymeric surface of the substrate material by radio frequency plasma treatment, the biocompatible polymeric material comprising substantially the same material as the polymeric substrate.

2. The method according to claim 1, wherein the polymeric substrate material is selected from the group consisting of polyacrylic acid, silicone elastomer, polypropylene, polyester, polyethylene terephthalate, polytetrafluoroethylene, polyurethane and polymethylmethacrylate.

3. The method according to claim 1, wherein the portion of the surface of the polymeric substrate material is removed by etching.

4. The method according to claim 3, wherein the etching is induced in a radio frequency plasma reactor.

5. The method according to claim 3, wherein the etching is induced in a radio frequency plasma reactor at a frequency of about 13.56 MHz.

6. The method according to claim 4, wherein the etching includes injecting a noble gas into the reactor.

7. The method according to claim 6, wherein the noble gas is argon.

8. The method according to claim 1, wherein the grafting is induced in a radio frequency plasma reactor generating a frequency of about 1 MHz to about 40 MHz.

9. The method according to claim 1, wherein the biocompatible polymeric material grafted to the substrate is selected from the group consisting of polymers of ethylenediamine, hexamethyldisiloxane, acrylic acid, diethylenetriamine, allylamine, hydroxyethylmethacrylate and methylmethacrylate.

10. A method of permanently modifying a surface of a polymeric substrate material, comprising the steps of:
    removing at least a portion of the surface of the polymeric substrate material; and
    subjecting the substrate surface to radio frequency plasma sufficient to raise the temperature at the substrate surface to just above the glass transition temperature of the substrate material surface for a time sufficient to produce a microscopically smooth, biocompatible surface on the substrate material.

11. The method according to claim 10, wherein the polymeric substrate material is selected from the group consisting of polyacrylic acid, silicone elastomer, polypropylene, polyester, polyethylene terephthalate, polytetrafluoroethylene, polyurethane and polymethylmethacrylate.

12. The method according to claim 10, wherein the portion of the surface of the polymeric substrate material is removed by etching.

13. The method according to claim 12, wherein the etching is induced in a radio frequency plasma reactor at a frequency of about 13.56 MHz.

14. The method according to claim 13, wherein the etching includes injecting a noble gas into the reactor.

15. The method according to claim 14, wherein the noble gas is argon.

16. The method according to claim 15, wherein the radio frequency plasma reactor operates at a power of about 100 watts to about 200 watts.

17. The method according to claim 10, further comprising covalently grafting a polymeric biocompatible material to the surface of the polymeric substrate material by radio frequency plasma treatment.

18. The method according to claim 17, wherein the grafting is induced in a radio frequency plasma reactor generating a frequency of about 1 MHz to about 40 MHz.

19. A method of manufacturing a prosthesis comprising the steps of:
    etching a surface of a polymeric presthesis core; and
    covalently grafting a polymeric biocompatible material to a surface of the core by radio frequency plasma treatment, whereby the prosthesis is provided with a microscopically smooth, biocompatible surface.

* * * * *